United States Patent
Teissl et al.

(10) Patent No.: US 6,348,070 B1
(45) Date of Patent: Feb. 19, 2002

(54) MAGNETIC-INTERFERENCE-FREE SURGICAL PROSTHESES

(75) Inventors: Christian Teissl, Innsbruck; Erwin Hochmair, Axams, both of (AT)

(73) Assignee: Med-El Elektromedizinische Gerate Ges.m.b.H (AT)

( * ) Notice: Subject to any disclaimer, the term of this patent is extended or adjusted under 35 U.S.C. 154(b) by 0 days.

(21) Appl. No.: 09/295,459

(22) Filed: Apr. 16, 1999

Related U.S. Application Data

(60) Provisional application No. 60/082,133, filed on Apr. 17, 1998.

(51) Int. Cl.[7] .............................. A61F 2/02; A61F 2/18
(52) U.S. Cl. ..................... 623/11.11; 623/10; 623/24; 600/12; 607/60
(58) Field of Search ..................... 623/10, 24, 11.11; 600/302, 423, 424, 12; 607/60

(56) References Cited

U.S. PATENT DOCUMENTS

| | | | | |
|---|---|---|---|---|
| 4,038,990 | A | * 8/1977 | Thompson | 607/9 |
| RE32,947 | E | 6/1989 | Dormer et al. | |
| 4,918,745 | A | 4/1990 | Hutchinson | |
| 5,456,654 | A | 10/1995 | Ball | |
| 5,554,096 | A | 9/1996 | Ball | |
| 5,630,835 | A | * 5/1997 | Brownlee | 607/60 |
| 5,716,407 | A | * 2/1998 | Knapp et al. | 128/898 |
| 5,749,912 | A | 5/1998 | Zhang | |
| 6,208,235 | B1 | * 3/2001 | Trontelj | 340/10.1 |

OTHER PUBLICATIONS

Brackmann et al., "Evaluation of MRI Compatibility of the Modified Nucleus Multichannel Auditory Brainstem and Cochlear Implants," *The American J. of Otology* 17(5):724–9, Sep. 1996.

Teissl et al., "Cochlear Implants: In Vitro Investigation of Electromagnetic Interference at MR Imaging—Compatibility and Safety Aspects," *Radiology* 208(3):700–8, Sep. 1998.

Teissl et al., "Magnetic Resonance Imaging and Cochlear Implants: Compatibility and Safety Aspects," *J. Magn. Reson. Imaging* 9(1):26–38, Jan., 1999.

* cited by examiner

*Primary Examiner*—David H. Willse
(74) *Attorney, Agent, or Firm*—Bromberg & Sunstein LLP

(57) ABSTRACT

Interference-free coil systems are coil systems having at least two coils which are identical in terms of inductance. These coils are arranged such that their magnetic fields are antiparallel to one another. Consequently, induced voltages within the coils are substantially eliminated when the coils are exposed to a homogeneous electromagnetic field. If exposed to an nonhomogeneous electromagnetic field, however, a net voltage is induced and enables the extraction of data and power. Reed switch configurations in the implantable prostheses protect against induced voltages caused by the radio frequency field generated by an MR imager when the reed switches are mounted parallel to the plane of a receiver. Reed switch configuration may be used to disconnect, de-tune, or short circuit a receiver. For example, they may be used to disconnect the receiver diodes. Some magnet configurations reduce torque caused by an external magnetic field and prevent demagnetization when disposed within, outside, or partially within an implantable prosthesis. Magnets which align with the external magnetic field also reduce the torque caused by the field and prevent demagnetization.

5 Claims, 6 Drawing Sheets

MAGNETIC-INTERFERENCE-FREE SURGICAL PROSTHESES

The present application claims priority from U.S. Provisional Application Serial No. 60/082,133 filed Apr. 17, 1998, which is incorporated herein by reference.

TECHNICAL FIELD

The present invention relates to surgical prostheses and external magnetic fields, and more particularly to apparatuses which will substantially eliminate induced voltages and torques produced when surgical implants are exposed to magnetic resonance imaging.

BACKGROUND ART

Cochlear implants (CIs) are an accepted means for the treatment of profound bilateral deafness by direct electrical stimulation of the auditory nerve. The majority of these systems consist of an external sound processing device and the actual implant, which is placed into an excavation of the outer lamina of the skull near the mastoid process. This implant includes circuitry for stimulation of the auditory nerve via electrodes inserted into the inner ear, and a receiver for the reception of radio frequency power and stimulation data via an inductively coupled coil system. Both stimulation information (selection of channel, stimulation pulse length, stimulation pulse level) and supply voltage are derived from the received signal. The demodulated signal is processed by a microprocessor that triggers a current source for stimulation. Excitable tissue in the inner ear is stimulated by current pulses generated by the implant electronics.

Small internal CI magnets are used to hold the external transmitter in place, and thus permit a sufficient transmission quality by holding the external transmitter in place. Typically, these mounting magnets are small, but strong, rare earth permanent magnets of cylindrical shape and magnetized in the main axis of symmetry, which is oriented normal to the skin.

Magnetic Resonance Imaging (MRI) has been the subject of staggering growth and development since its introduction in 1973. Like many other imaging techniques being used in medicine, MRI takes advantage of an interaction between an external electromagnetic field and the human body. In contrast to Computed Tomography, MRI uses a long (greater than 0.3 meters in wavelength), nonionizing radio frequency window of the electromagnetic spectrum to probe the body. Therefore, a resulting limit to the spatial resolution has to be overcome by superimposing two fields, a radio frequency field, which is used to change the energy states of the protons, and a spatially varying static magnetic field. For practical reasons, this spatially varying static magnetic field is generated by adding a moderate strength static magnetic field, which is used to align the hydrogen atoms, and three small, rapidly time-varying magnetic field gradients impressed upon these static fields, which are used for spatial localization.

Using this principle, the patient is spared exposure to potentially harmful doses of radiation. The images produced using MRI are of higher resolution and clarity than those produced by Computed Tomography. Furthermore, MRI is gaining more and more significance as a key medical application. As such, MRI has become a widely used testing component, posing little risk to the majority of patients undergoing MRI scans.

Cochlear implants and MRI have become widely used in recent years. To date, more than 18,000 CIs have been implanted. Moreover, an increasing number of Auditory Brainstem Implant users has to be considered. MRI rather than Computed Tomography, is the preferred imaging method for post operative check-ups. Subsequently, it is very likely that CI wearers will, at some point in their life, become candidates for MRI examinations.

Unfortunately, the different magnetic fields appearing during MRI interfere with the implant. Eddy currents in conductive elements of the CI can produce heat which may burn the surrounding tissue. Induced voltages in conductive loops resulting from the radio frequency field can damage the implant. Force and torque on ferromagnetic parts of the implant which occur because of magnetic field gradients and the homogeneous magnetic field, can produce pain, hurt the patient, or impede the implant's functionality. Furthermore, the small mounting magnets can be partially demagnetized, resulting in reduced implant functionality.

With implanted devices, power and data can be transmitted transcutaneously via an inductive link by means of an inductively coupled coil system. Such a coil system may consist of a primary coil, which is outside the body, and a secondary coil implanted with the cochlear stimulator. When facing each other, they form a transformer that allows energy transfer from the transmitter to the implant.

The choice of the carrier frequency for transcutaneous links for implantable devices is governed by two considerations: absorption in the tissue, if power efficiency has to be considered, and compactness of the implant. This restricts usable frequencies to a range of approximately 2 to 50 MHZ. However, these same carrier frequencies are also within the range of the transmitter frequencies of common MRI units (2.2 MHZ at 0.05 T to 82.2 MHZ at 2.0 T). Consequently, the transmitted radio frequency pulses of the MRI unit leads to induced voltages in implanted receiver coils. The induced voltage intensity depends on: 1) the difference between the frequency of the receiver tuned circuit of the implant and the frequency transmitted from the MRI unit; 2) the bandwidth of the receiver tuned circuit and of the transmitted radio frequency pulse, and 3) the radio frequency peak power of the transmitted radio frequency pulse of the MRI unit which, in turn, depends on the field strength of the unit, the flip angle, the pulse duration, and the envelope of the pulse.

With multi-channel digital implanted systems, the implanted receiver tuned circuit will be connected to the implant electronics, which has a maximum allowed input voltage. Exceeding this voltage can lead to the destruction of the implant. In contrast to these digital systems, the induced signal in single-channel analog implants may reach the electrodes, which can lead to unintended stimulation signals, possibly resulting in overstimulation of the auditory nerve or destroyed nerve fibers.

Torque is exerted on an implanted device by the static magnetic field of the MRI unit. It is proportional to the field strength and the magnetization components lying orthogonal to the direction of the field. Common high field MRI units use superconductive magnets to produce a comparable strong magnetic field to flip the spins of the protons. These magnetic fields can exert a strong torque on implanted magnets, especially if the magnetic moment of the implanted magnet is perpendicular to the longitudinal main magnetic field of the scanner. The associated risk for the patient includes the possibility that the implant will turn and exert pressure on the brain, that the implant will dislodge, that there will be mechanical trauma to surrounding tissue, and that the electrode leads will be damaged by shear forces which could cause a partial or total loss of implant functionality.

A simple solution to prevent the interference between the internal CI magnet and the MRI unit is to omit the internal CI magnet. This can be realized by utilizing a completely magnetless CI, which is offered by the main CI manufacturers, and holding the external receiver in place by an ear-hook. This is an optimal CI for an MRI unit, but it is not as comfortable for the patient, especially for children, as the devices incorporating internal magnets.

There is of course the possibility of removing the magnet. This is done by an ambulant procedure prior to the MRI examination. One disadvantage of this design change is that, because the magnet has to be easily removable, it is also insecurely fixed and would probably have to be removed before any MRI examination, regardless of the magnetic field strength of the unit. Another disadvantage is that, because of the healing process which must follow removal, the CI patient is not able to use the device for a period of time after the procedure.

SUMMARY OF THE INVENTION

In accordance with the preferred embodiments of the invention there is provided an inductively coupled coil system of an implantable prosthesis for receiving electromagnetic waves from an external transmitter, the system comprising at least two coils of identical inductance, the coils connected such that the winding direction of one coil is antiparallel to the winding direction of the other coil.

In accordance with a further embodiment, the coil system receives both power and stimulation data from an external transmitter. In accordance with a further embodiment, the at least two coils are formed by dividing an existing coil into at least two coils of identical area. In accordance with another embodiment, at least one coil is positioned outside a housing of an existing coil, the positioned coil and the existing coil having identical areas. In accordance with a further embodiment, the implantable prosthesis has a housing and at least one coil is located on a front face of the housing and at least one coil of identical area is located on a back face of the housing. In another embodiment, the coil system is used to send electromagnetic waves to an implantable prosthesis. In a further embodiment, the coil system sends both power and stimulation data to an implantable prosthesis.

Also provided is a reed switch system of an implantable prosthesis for providing overvoltage protection in the presence of a magnetic field, the system comprising at least one magnetic reed switch, the reed switch capable of being activated by a magnetic field external to the implantable prosthesis. In a further embodiment, the reed switch system is mounted parallel to the plane of a receiver. In another alternative embodiment, the reed switch system is used to disconnect, de-tune, or short circuit a receiver. In another embodiment, the reed switch system is used to disconnect a receiver's diodes or other components in a current path.

Also provided is a magnet system of an implantable prosthesis for reducing torque exerted by an external magnetic field and preventing demagnetization, the system comprising at least two magnets, the magnets having antiparallel magnetic moments of identical magnitude. In a further embodiment, the magnets are mounted within the implanted prosthesis. In an alternative embodiment, the magnets are mounted outside of the implanted prosthesis. In another embodiment, the magnets are mounted partially within the implanted prosthesis. In a further embodiment, the magnets are disposed within a transmitter.

There is also provided a magnet system of an implantable prosthesis for reducing torque exerted by an external magnetic field and preventing demagnetization, the system comprising at least one magnet, the magnet disposed within the prosthesis such that it aligns with the external magnetic field.

BRIEF DESCRIPTION OF THE DRAWINGS

The present invention will be more readily understood by reference to the following detailed description taken with the accompanying drawings, in which.

DETAILED DESCRIPTION OF SPECIFIC EMBODIMENTS

Embodiments of the invention address two sources of interference that are considered disadvantageous to the function of hearing prostheses: 1) the induced voltages in coils and tuned circuits due to the radio frequency field generated by MRI units; and 2) the torque on magnets generated due to the static magnetic field of MRI units.

An interference-free coil system for a surgical implant has at least two coils, which are identical in terms of inductance. Any induced voltage due to a homogeneous radio frequency field in the individual coils will be equal, and if connected according to a preferred embodiment of this invention, the individual voltages of the coils will compensate each other. Consequently, such an arrangement results in the substantial elimination of residual signals produced when the system is exposed to a homogeneous electromagnetic field such as from a head or body resonator of an MRI unit. On the other hand, if exposed to an nonhomogeneous electromagnetic field such as the radio frequency field of a small radio frequency transmitter associated with a cochlear implant system, a net voltage is induced enabling the extraction of data and the gaining of power.

Figure 1:
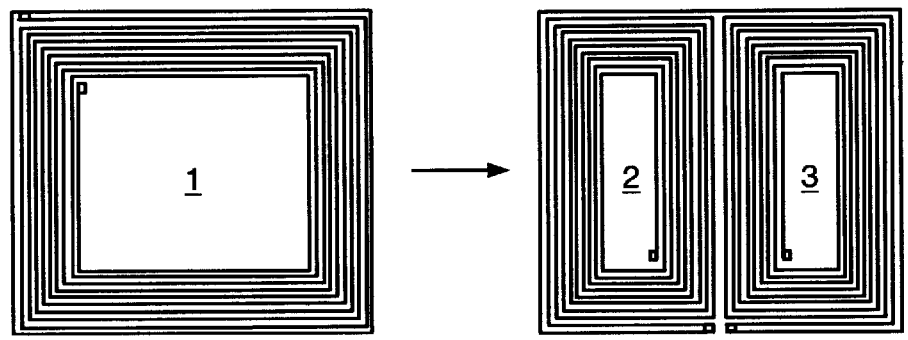
FIG. 1 is an illustration of one embodiment for an interference-free coil system.
Figure 2A:
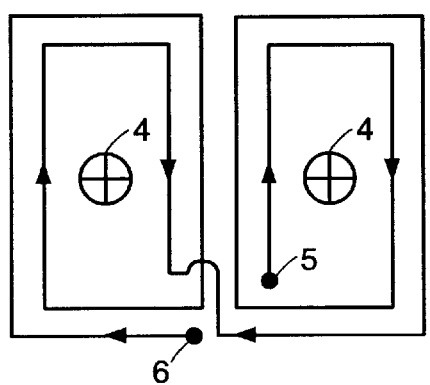
FIG. 2(a) is a schematic illustration of the principle of interference-free coil systems in the presence of a homogeneous radio frequency field.
Figure 2B:
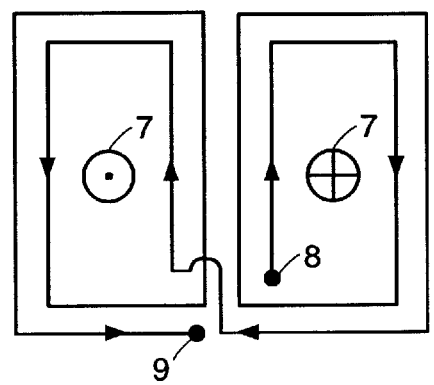
FIG. 2(b) is a schematic illustration of the principle of interference-free coil systems in the presence of opposing radio frequency fields.

A preferred embodiment of the present invention includes a system for interference-free coils as illustrated in FIG. 1 wherein the area of a conventional receiver coil 1 of area A is divided into two coils 2 and 3, each of area A/2. To realize the interference-free coil system, the two coils are connected such that their magnetic fields are antiparallel as illustrated in FIG. 2. The symbols ⊕ and ⊙ respectively depict a radio frequency magnetic field vector directed into and out of the drawing plane. FIG. 2(a) illustrates the coil system in the presence of a homogeneous radio frequency field 4, the induced voltages between the terminals 5 and 6 in the new coil configuration compensate each other if the two inductances are identical. FIG. 2(*b*) illustrates that the application of opposing radio frequency fields 7 by an external transmitter, which contains an identical coil system, results in an induced voltage between the terminals 8 and 9, which is the sum of the two individual voltages. This arrangement requires more accurate positioning of the coils, since this arrangement has increased sensitivity to lateral displacement. A higher current in the transmitter coil may need to be used because this arrangement's coupling coefficient is decreased by a factor of two.

Figure 3:
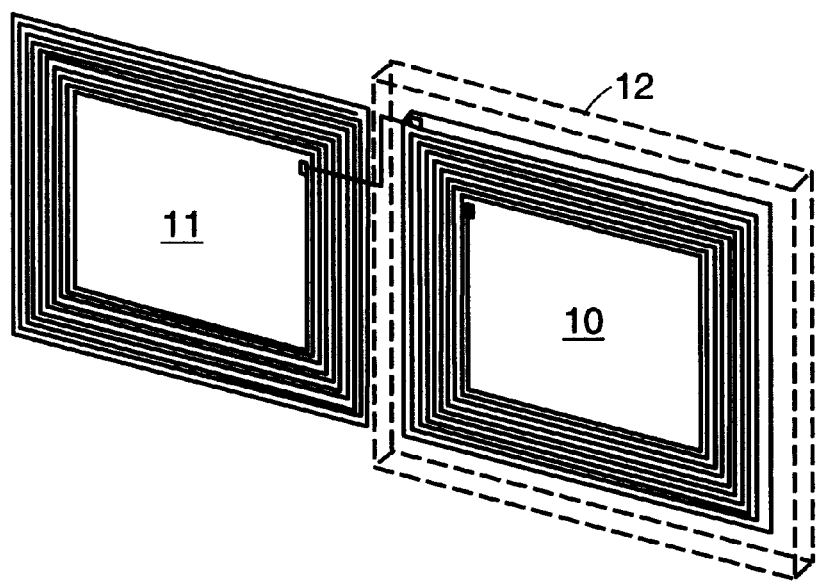
FIG. 3 is an illustration of a second embodiment for an interference-free coil system.

Another preferred embodiment of the present invention is illustrated in FIG. 3 wherein the original coil area of a conventional receiver or transmitter 10 is retained and a coil of identical inductance (e.g., identical area) 11 is added. One way to implement this solution without design changes is to position an insulated coil outside an implant housing 12. Printed coils can be manufactured on very thin films, consequently, this positioning would not be a problem. This system is not as sensitive to lateral displacement as the system shown in FIG. 2, and the coupling coefficient is comparable to that of the original receiver coil.

Figure 4:
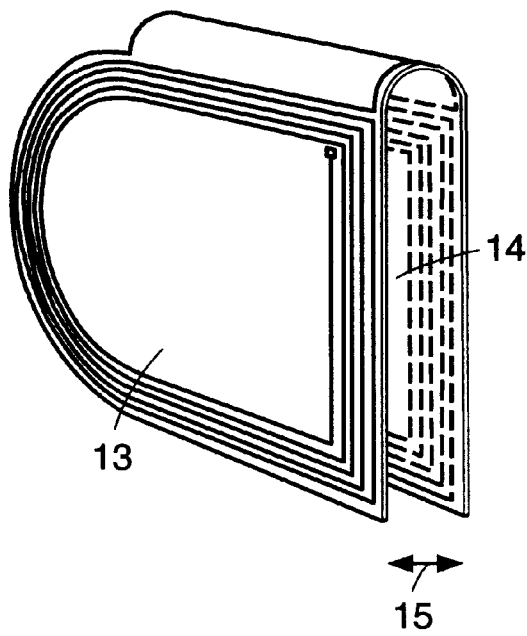
FIG. 4 is an illustration of a third embodiment for an interference-free coil system.

A third preferred embodiment of the present invention is illustrated in FIG. 4 wherein the induced voltage in the implant receiver circuit is reduced by retaining the conventional coil area and mounting a coil 13 to the front face of the implant housing and a coil 14 of identical inductance (e.g., identical area) to the back face of the implant housing. Within the comparable homogeneous radio frequency magnetic field of the MRI unit, the sum of the two induced component voltages is equal to zero, whereas the nonhomogeneous radio frequency field generated by the external transmitter produces a net-voltage which depends on the distance 15 between the two coils. This system is especially suitable for thicker implants.

Preferred embodiments for interference-free coil systems cover any configuration wherein the individual inductances of the two subcoils are equal and the individual coils are properly aligned. The coil systems of the receiver should have the same coupling to the interfering radio frequency magnetic field. This condition can be achieved by many different ways, independent of coil shape, type of coil, number of coils, or number of windings. For example, for some applications it may be beneficial to decrease the area of the additional coil or coils and to increase the number of windings.

Figure 6:
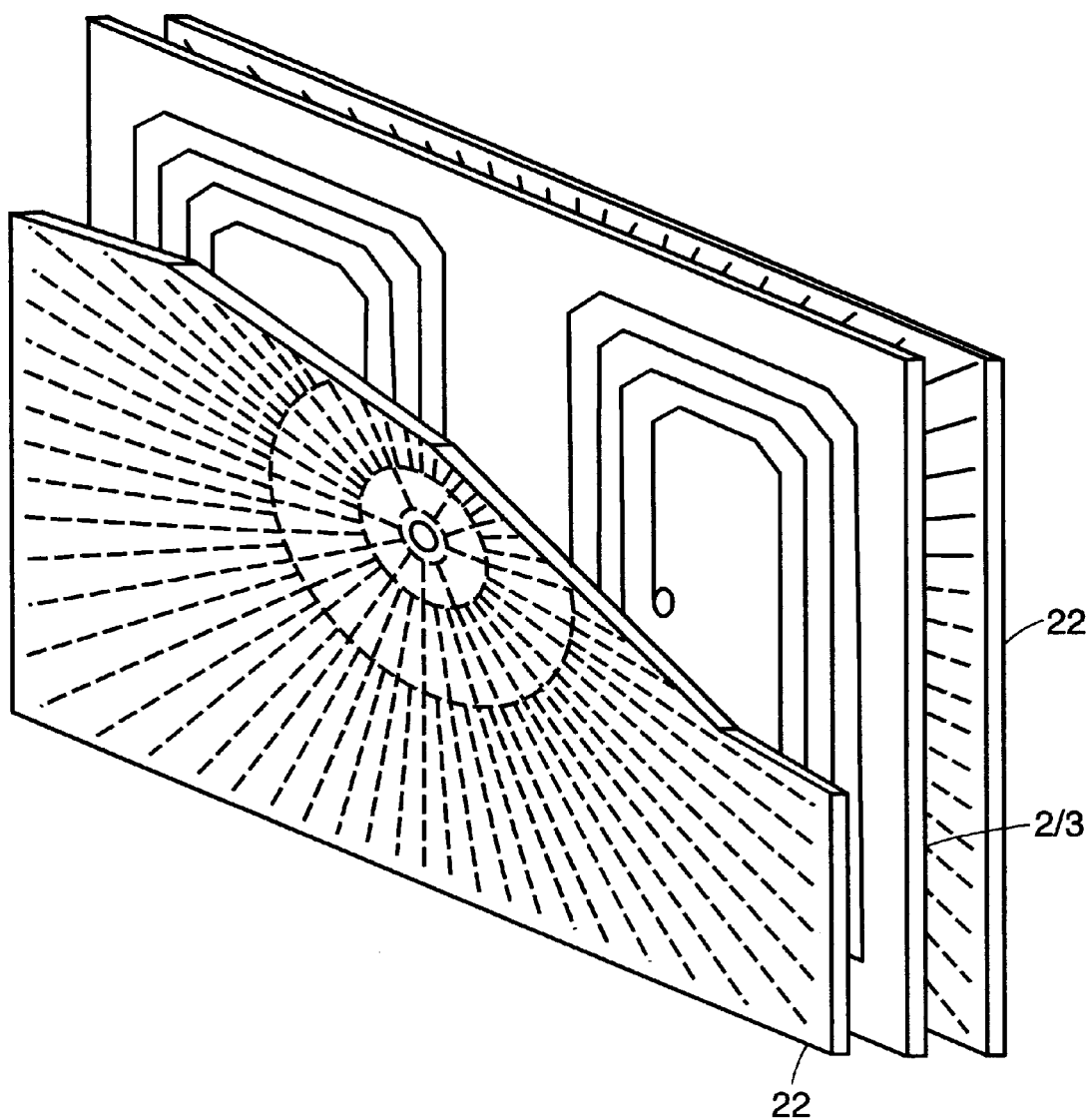
FIG. 6 is an illustration of a shielded interference-free coil system.

A capacitive coupling between the partial coils of the interference-free coil configuration and the coils of the head or the body resonator of the MRI unit can also lead to a residual voltage, but this can be avoided by shielding the interference-free coil system as shown in FIG. 6. The shielding 22 avoids capacitive coupling between the interference-free coil system ⅔ and the head or body resonator.

Figure 5:
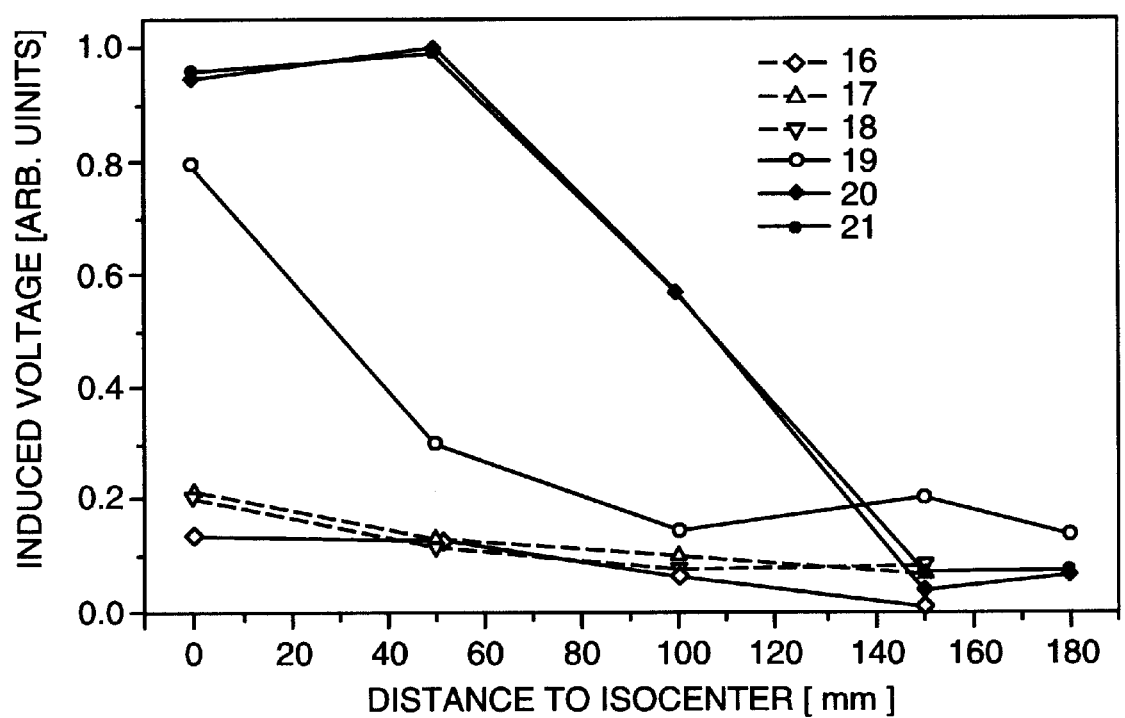
FIG. 5 is a graphic illustration of induced voltage resulting from various coil configurations.

Preferred embodiments of interference-free coil systems are capable of strongly reducing the induced voltage in implanted coils in a consistent manner by means of a compensation effect as illustrated in FIG. 5. The graph shows the voltage induced in various coil systems with respect to the distance of the coil system from the isocenter of the MR imager. Radio frequency pulses with a high intensity were used to induce high peak voltages. The coils were placed in the worst-case orientation. Graph line 16 illustrates the induced voltage in a shielded interference-free coil system as described in this disclosure. Graph line 17 illustrates the induced voltage in a partially shielded interference-free coil system. Graph line 18 illustrates the induced voltage in a partially shielded interference-free coil system rotated ninety degrees. Graph line 19 illustrates the induced voltage in a non-shielded interference-free coil system. Graph line 20 illustrates a shielded reference coil. Graph line 21 illustrates a non-shielded reference coil. Induced voltages are substantially eliminated when the interference-free coil systems of this invention are used regardless of the interference-free coil system's distance from the isocenter of the external magnetic field. Residual signals are decreasing with decreasing geometrical size of the implanted coils and with increasing homogeneity of the transmitted radio frequency field.

To further enhance the safety of a patient, a simple but efficient overvoltage protection in the receiver can be realized by reed switches. If a certain individual minimum threshold level is exceeded, which can be as low as 15 gauss, a reed switch will either close in a static magnetic field and create a short in the receiver coil or will open in the magnetic field and thus disconnect the receiver coil from the rest of the circuit or switch off the other components, such as the receiver diodes.

For the design of an overvoltage protection by means of reed switches, the different MRI magnet types have to be considered because with different magnet types, the main magnetic field vector can either point in x, y, or z direction. The radio frequency field can be linearly polarized or circularly polarized, but is always oriented perpendicular to the main magnetic field vector. Therefore the number of reed switches can be decreased to two reeds or even one reed, depending on the individual application.

Figure 7:
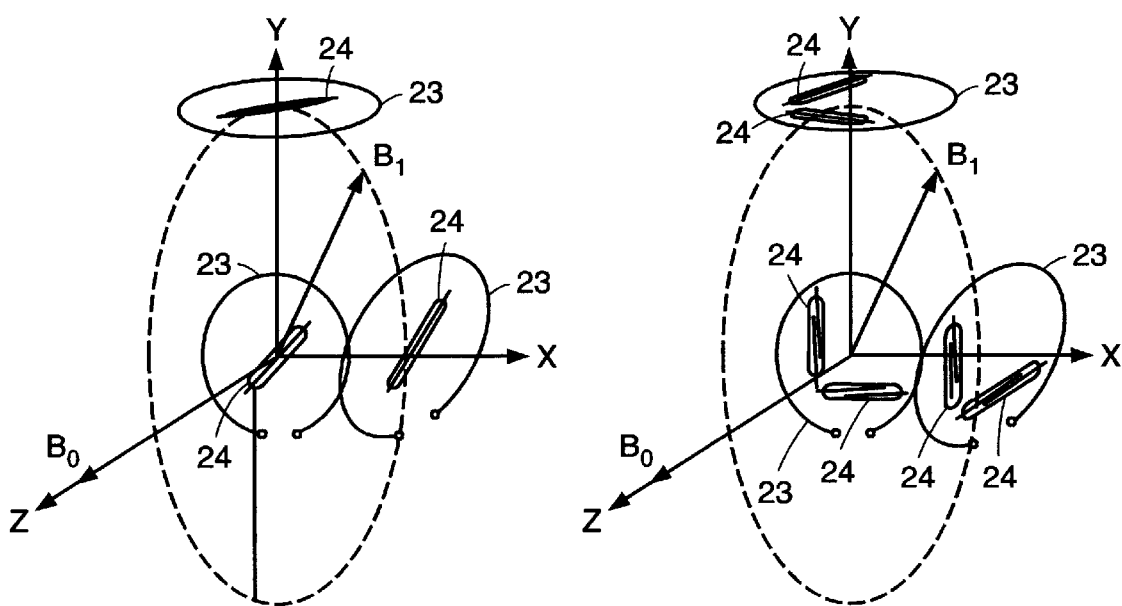
FIG. 7 is an illustration of reed switches mounted parallel to the plane of the receiver.

A preferred embodiment of the above application is illustrated in FIG. 7 wherein $B_0$ represents the static magnetic field produced by the MRI unit and $B_1$ represents the radio frequency field. Protection against induced voltages in a closed loop, coil, or its equivalent 23 is accomplished by at least one reed switch 24. If the reed switch 24 is mounted parallel to the plane of the closed loop 23, no third reed switch is needed because almost no signal will be induced having the loop or coil plane perpendicular to $B_0$. One possibility would be to orientate the reed switch or switches within the plane of the receiver. In this arrangement, the reeds will not switch if the loop or coil plane is perpendicular to $B_0$, however this has no consequence because there is no induced voltage with this configuration. Protection of the connected circuit can be realized by either short-circuit, de-tune, or disconnection of the receiver or other components in the current path. The reed switches have to be selected and arranged in such a way as not to be activated by either the internal magnet of the implant or by the magnet of the transmitter.

MRI-safe magnets are also realized by using a compensation effect. The exerted torques on two magnets that are identical in terms of their magnetic moments in a homogeneous magnetic field is equal. Consequently, the total torque on an implant housing can be substantially reduced by using at least two magnets with antiparallel magnetic moments. The two individual torques will compensate each other.

Figure 8:
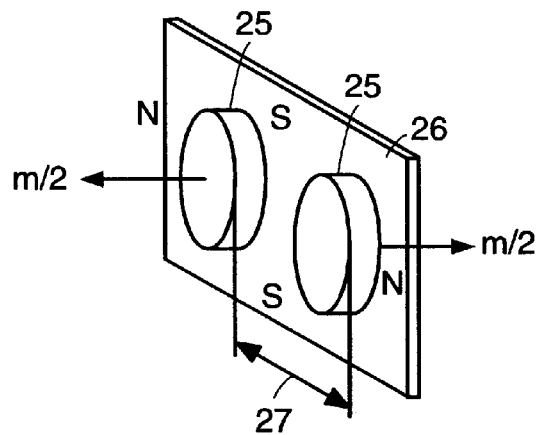
FIG. 8 is an illustration of two rare earth magnets with anti-parallel magnetic moments.

A preferred embodiment of this magnet configuration is illustrated in FIG. 8. Two rare earth magnets 25 with antiparallel magnetic moments m/2 and −m/2 are fixed on the substrate of the implant 26 at a distance 27. The resulting torque within a homogeneous magnetic field is zero. Such homogeneous magnetic fields are present in the imaging area, or isocenter, of an MRI unit, where $B_0$ reaches its maximum. On the other hand, if the described magnet arrangement is exposed to an nonhomogeneous magnetic field such as one generated by an external magnet configuration similar to the internal magnet configuration, an attractive force results. Consequently, this design will reduce the torque over the whole area of the static magnetic field of the MRI unit to negligible values.

Figure 9:
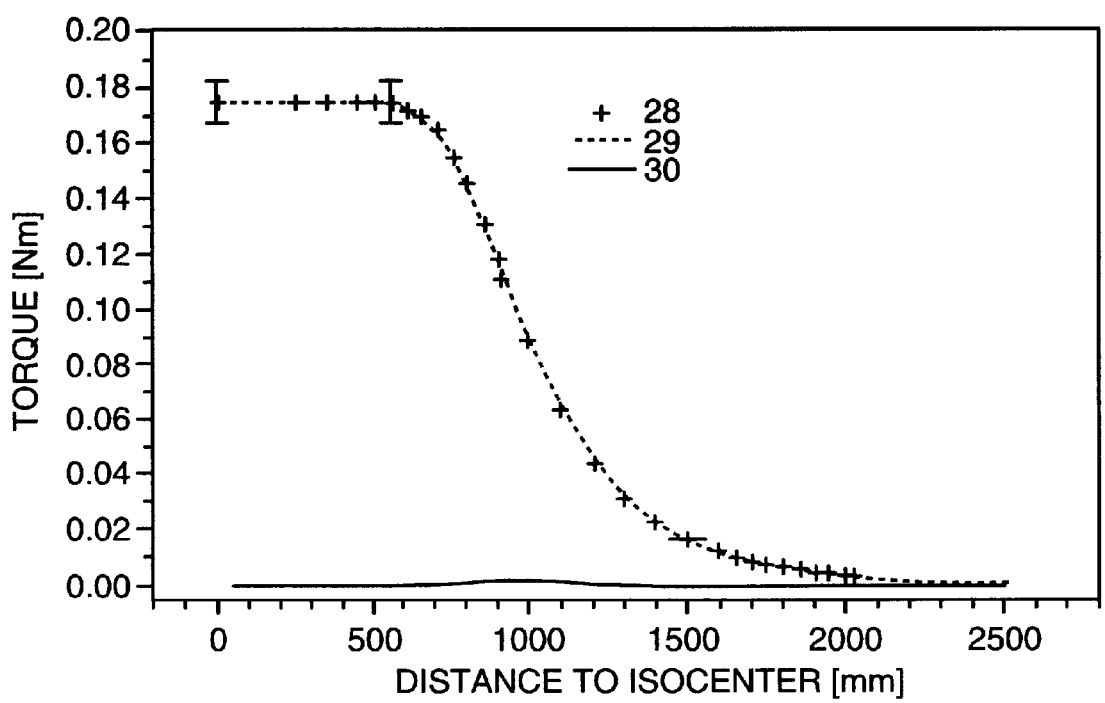
FIG. 9 is a graphic illustration which compares the torque exerted on a conventional magnet and the torque exerted on the MRI-safe magnet system.

Since the dimensions of common implanted systems are comparatively small, the distance between the two internal magnets is small, and the residual torque on this arrangement will also be negligible in the fringe field of the MRI unit as illustrated in FIG. 9 wherein the measured torque on a conventional internal magnet is shown as a function of the distance to the isocenter with the magnetic moment perpendicular to the static magnetic field $B_0$. Line 28 represents the torque as a function of the isocenter in the conventional head position. The dotted line 29 represents the calculated torque with the measured scanner magnetic field and the magnetic moment of the internal CI magnet. The CI magnet has a magnetic moment of 0.11691 Nm/T. Line 30 represents the calculated torque for the interference-free magnet configuration disclosed in this specification with a distance 27 of 11 millimeters between the two magnets. An added advantage of this configuration is that the two internal magnets would be less sensitive to partial demagnetization because of a more suitable ratio of the magnet dimensions.

It should be noted that it has been contemplated that in a further embodiment of the present invention, the total torque on a magnet of the implant may be reduced to residual values, and partial demagnetization may be prevented, by enabling the magnet to align with an external magnetic field.

What is claimed is:

1. A coil system in an implantable prosthesis for receiving electromagnetic waves from an external transmitter, the system comprising:

two coils of identical inductance, adapted to be positioned substantially equidistant from the external transmitter, the coils connected such that the winding direction of one coil is antiparallel to the winding direction of the other coil, and such that the sum of the voltages induced in the coils by a homogeneous electromagnetic field is substantially equal to zero.

2. A coil system according to claim 1, wherein the system receives both power and stimulation data from an external transmitter.

3. A coil system according to claim 2, wherein at least one coil is positioned outside a housing of an existing coil, the positioned coil and the existing coil having identical areas.

4. A coil system according to claim 1, wherein the system is adapted to operate at a frequency:

(a) greater than or equal to 2 MHz, and (b) less than or equal to 50 MHz.

5. A coil system according to claim 1, further including a magnetic reed switch arrangement for providing overvoltage protection in the presence of a magnetic field.

* * * * *